United States Patent [19]

Kolbe et al.

[11] Patent Number: 5,038,772

[45] Date of Patent: Aug. 13, 1991

[54] CLOSED-CYCLE BREATHING EQUIPMENT

[75] Inventors: Ernst-Günther Kolbe, Molln; Norbert Kollenbrandt, Berkenthin; Hasso Weinmann, Lubeck; Wolfgang Drews, Zarpen; Karsten Vogeler, Brunsbeck; Hans-Burkhardt Fiedler, Lubeck, all of Fed. Rep. of Germany

[73] Assignee: Drägerwerk Aktiengessellschaft, United Kingdom

[21] Appl. No.: 368,870

[22] Filed: Jun. 20, 1989

[30] Foreign Application Priority Data

Jul. 9, 1988 [DE] Fed. Rep. of Germany ....... 3823382

[51] Int. Cl.[5] ............................................ A61M 16/00

[52] U.S. Cl. ........................... 128/205.14; 128/205.16

[58] Field of Search ...................... 128/205.13, 205.14, 128/205.16, 204.18

[56] References Cited

U.S. PATENT DOCUMENTS

| | | | |
|---|---|---|---|
| 4,060,077 | 11/1977 | Friedman | 128/205.16 |
| 4,224,940 | 9/1980 | Monnier | 128/205.16 |
| 4,498,470 | 2/1985 | Warncke | 128/202.26 |
| 4,928,685 | 5/1990 | Gray | 128/204.24 |

FOREIGN PATENT DOCUMENTS

| | | | |
|---|---|---|---|
| 2045494 | 3/1971 | Fed. Rep. of Germany | 128/205.16 |
| 1393311 | 2/1965 | France | 128/205.16 |
| 2366833 | 5/1978 | France | 128/205.16 |
| 900866 | 7/1976 | United Kingdom | 128/205.16 |

*Primary Examiner*—Clifford D. Crowder
*Assistant Examiner*—E. P. Raciti
*Attorney, Agent, or Firm*—McGlew & Tuttle

[57] ABSTRACT

A closed-cycle breathing equipment and gas mask for operation under pressure with a pressurized air source for respiratory air and with an air bag being under prestress during the inspiration phase includes an arrangement where the prestress is decreased by a control element recognizing the expiratory phase and so as to support respiration during the expiration phase. A pneumatic control valve is used which can switch connections between the inspiration and the expiration phase and which is directly controlled by the difference between the exhalation pressure and the pressure in the air bag. The control valve connects the pressurized air source with the air bag during the inspiration phase and during the expiration phase it interrupts the connection due to the occurring dynamic pressure of the pressurized air from the pressurized air source and thus actuates a pneumatic adjusting element so that the mechanical prestress at the air bag is reduced.

11 Claims, 1 Drawing Sheet

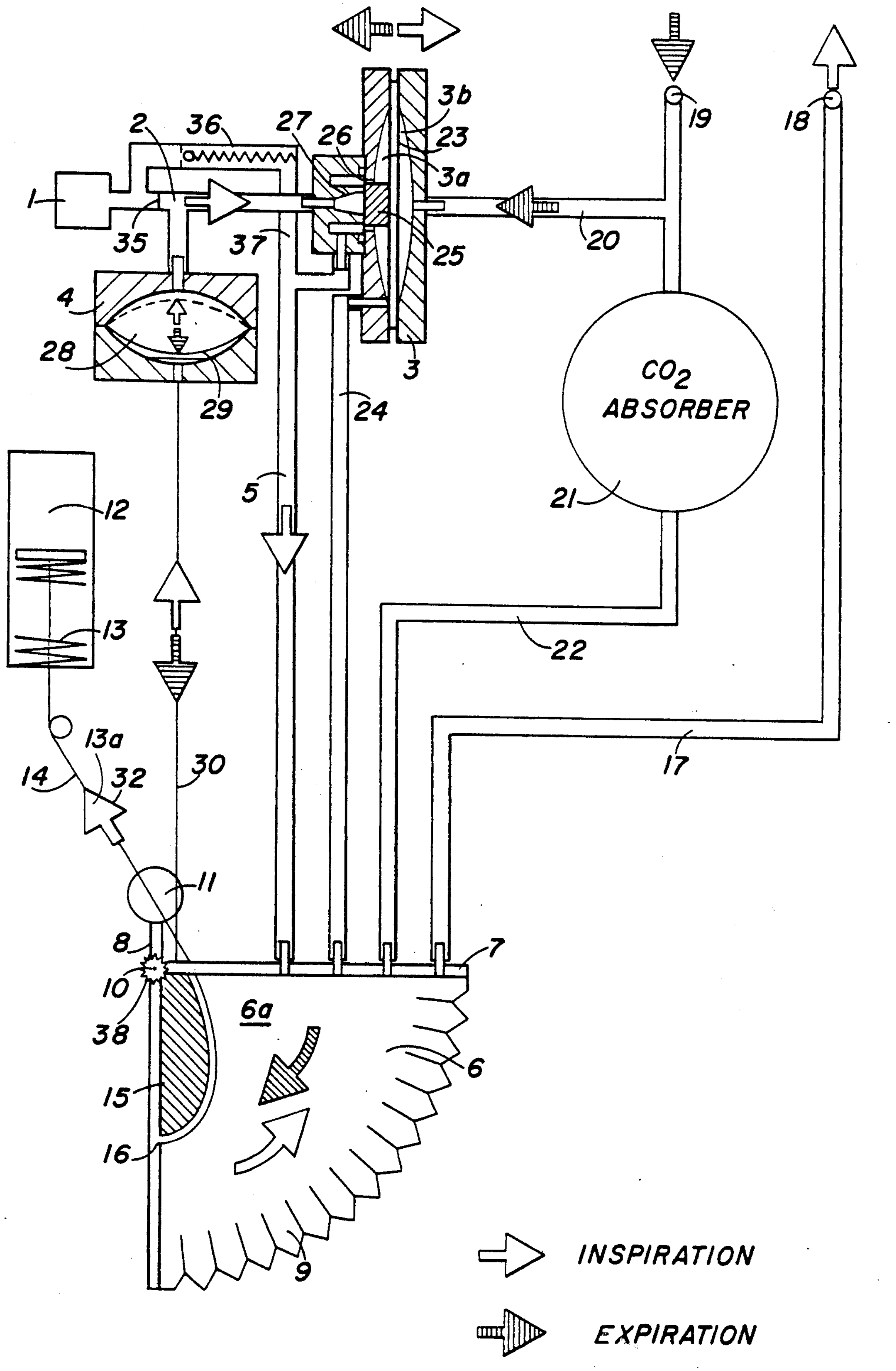
1
2
3
3a
3b
4
5
6
6a
7
8
9
10
11
12
13
13a
14
15
16
17
18
19
20
21
22
23
24
25
26
27
28
29
30
32
35
36
37
38
$CO_2$ ABSORBER
INSPIRATION
EXPIRATION

CLOSED-CYCLE BREATHING EQUIPMENT

BACKGROUND OF THE INVENTION

1. Field of the Invention

The invention relates in general to respirators and in particular to a new and useful closed-cycle breathing apparatus and gas mask for operation under pressure with a pressurized gas source supplying respiratory air and with an air bag being under prestress during the inspiration phase, and prestress means for prestressing the airbag said prestress means decreasing the amount of prestressing applied or decreasing the degree of prestress by means of a control element recognizing the expiratory phase, to thereby support the respiration during the expiration phase.

In a closed-cycle breathing apparatus and gas mask for operation under pressure it is guaranteed that the pressure in the breathing cycle is constant with regard to the surrounding atmosphere, so that no pollutants can enter the breathing cycle. The pressure applied by the prestress means can be generated by an elastic element for prestressing the air bag, by means of a mechanical/ pneumatic spring, such as is represented e.g. in German Patent DE-PS 31 05 637. As the prestressing of the air bag generated by the mechanical and pneumatic spring, is also maintained during the exhalation process, exhalation in such a system is rendered even more difficult due to the flow resistance to be overcome during the expansion in the expiration phase. The breathing resistance tends to increase.

From German Patent DE-OS 34 29 345 a closed-cycle breathing apparatus is known and a gas mask for operation under pressure wherein the pressurized gas source also supplies an auxiliary device increasing the mechanical prestressing of the air bag to achieve an increase in pressure. A detector connected to a measuring circuit differentiates between the respiratory phases and controls the auxiliary device during the exhalation phase so that the additional pressure exerted on the air bag is reduced.

In certain cases a simplified execution of the breathing support is desirable which is based exclusively on pneumatic/ mechanical elements without electronic control circuitry and without an additional electrical energy source.

SUMMARY OF THE INVENTION

The invention permits the adjusting of a closed-circuit gas mask and breathing equipment in a simple way so as to support the breathing in the inspiration and in the expiration phase of the breathing cycle.

According to the invention a pneumatic control valve is provided which switches between the inspiration and the expiration phase and is directly controlled by the difference between the exhalation pressure and the pressure in the air bag. The control valve connects the pressurized air source with the air bag during the inspiration phase and during the expiration phase it interrupts the connection due to the occurring dynamic pressure of the pressurized air from the pressurized air source and thus actuates a pneumatic adjusting element so that the mechanical pressure applied or prestress of the air bag is reduced.

Actuation elements of various shapes can be used as pneumatic adjusting elements, e.g. a bellows, a membrane, a cylinder unit or such like.

Therefore, in the inspiration phase the maintenance of the pressure in the breathing cycle and a certain breathing support are generated by the air bag being prestressed. The expiration phase is recognized by the control valve so that only now the compensation for this prestress is triggered. For this purpose the dynamic pressure of the pressurized air actuates the pneumatic adjusting element, which, in turn, acts immediately and mechanically upon a part of the air bag wall and influences it in direction of an increase in volume. Therefore the energy of the continually flowing respiratory air is used to decrease or nearly eliminate the applied pressure or prestress of the air bag during the expiration phase.

A further advantage can possibly be achieved by providing a mechanical prestress means having a spring element for prestressing or applying to the air bag. Advantageously the air bag is provided with a pressure-exerting movable pivoting wall as one of its wall-parts which is connected to the spring element. The transmission of force from the pivoting wall via a curved plate is executed so that the supply pressure of the air bag is at least approximately constant regardless of its filling ratio. The control valve, the pneumatic adjustment element, the air bag and the chosen prestress are coordinated so that forced respiration cannot take place although a set positive pressure prevails in the respiratory cycle at all times.

In order to render the described prestress position-independent, the pivoting wall exerting pressure on the air bag is provided with a counterbalance weight on the side opposite the point of rotation.

Favorably the pneumatic control valve is executed as a double membrane valve wherein a control membrane transmits the difference between exhalation pressure and the pressure in the air bag onto a switch membrane which switches the pressurized air flow between the air bag during the inspiration phase and the pneumatic control element during the expiration phase.

In an advantageous embodiment the exhalation pressure is received as dynamic pressure by a component generating a considerable exhalation resistance. The exhalation pressure can therefore be received as dynamic pressure e.g. in front of the absorption bed of the respiratory air cartridge binding the carbon dioxide or in front of the respiratory lines.

In a favorable evolutionary development, the pneumatic adjustment element transfers a moment opposing the pulling force of the spring element to the pivoting wall of the air bag by means of a mechanical coupling element. This can e.g. be done by providing the coupling element with a flexible end being connected to the axis of the pivoting wall while partially embracing the axis. The flexible end can have the shape of a rope if the working stroke of the adjustment element is a pulling stroke, or a leaf spring if the working stroke is a pushing stroke.

In another advantageous embodiment a membrane is arranged in the adjustment element which actuates a toothed wheel arranged on the rotation point of the pivoting wall by means of a toothed rod.

A smoothing device ensures that possibly occurring oscillations in the pressure of the respiratory air supply source do not result in an untimely actuation of the adjustment element. The pressure release valve gives an upper limit for the dynamic pressure of the pressurized air. When the control valve is open, the throttle releases a constant respiratory air flow, the flow pressure decreasing to a value which relaxes the adjustment valve. The amount of gas being discharged at the pressure release valve is preferably fed into the air bag.

Accordingly, it is an object of the invention to provide a respiratory gas breathing device including a respiratory air delivery bag connected to both an inspiration line which is connected to a patient and an expiration line from the patient back to a bellows type breathing bag which has a member which is movable to provide a flow of the respiratory gas for inhalation gas flow and in another operational direction to effect a flow of gas back to the bellows. It forms a breathing bag in which includes a control which senses the inspiration pressure in relation to the expiration pressure and controls an element for prestressing the bellows so that it recognizes the expiration phase of breathing and supports the respiration during this expiration phase while still providing for prestressed inspiration.

A further object of the invention is to provide a respirator which is simple in design, rugged in construction, and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWINGS

In the drawings:

The only figure of the drawings is a schematic showing of a closed cycle breathing device constructed in accordance with the invention.

DESCRIPTION OF THE PREFERRED EMBODIMENT

A pressurized air source 1 supplying the respiratory air is connected to a double membrane or double diaphragm valve 3 serving as the pneumatic control valve and to a pneumatic adjusting element 4. An air supply line 5 of the double membrane valve 3 opens into an air bag 6 having the shape of a bellows 9.

The throttle (35) of a smoothing device is mounted between the pressurized air source 1 and the connection line 2. A pressure relief valve 36 branches off from the throttle 35, the discharge opening of the valve 36 opening into the gas supply line 5 by way of a discharge line 37.

The air bag 6 comprises a fixed wall part 7 on which the accordion-shaped bellows 9 is fixed by means of a movable pivoting wall 8. The pivoting wall 8 has a balancing weight 11 on the side opposite the rotation point 10.

A spring element a prestress means 12 is provided for the prestressing of the air bag 6. The prestress means generates a prestress or an initially applied force by means of a pressure spring 13. The prestress pressure acts upon a working point 16 on the pivoting wall 8 of the air bag 6 by means of a mechanical pull connection 14 via a cam plate 15.

An inhalation line 17 leads from the air bag 6 to the inhalation connection 18 of a breathing mask or mouthpiece which is not shown in the drawing.

An exhalation connection 19 of the mask is connected to a chalk board 21 for $CO_2$ absorption through a feed line 20 which is also branched. A recycling line 22 for the respiratory air connects the or $CO_2$ absorber 21 with the interior of the air bag 6.

The branched-off supply line 20 is connected to a partial chamber in front of a control membrane 23 in the double membrane valve 3. The control membrane 23 is connected so as to define respective partial chambers **3*a* and 3*b* on respective sides. Chamber 3*a* is connected to the inner chamber of the air bag by means of a pressure control line 24. A check block 25 is connected to the control membrane 23 of the double membrane valve 3 and lies close to a switch membrane 26 which it pushes against a valve seat 27 for the opening of the connection line 2 toward the gas supply line 5. Herein, the control membrane 23** serves as the control element recognizing the breathing phase.

The pneumatic adjusting element 4 has an expansion chamber 28 in which an arched membrane 29 extends. The membrane 29 is connected to the movable pivoting wall 8 by means of a mechanical coupling element 30, so that during the expiration phase a force is exerted on the movable pivoting wall 8, which releases at least a part of the prestress generated by the pressure spring 13 during the inspiration phase.

During the inspiration phase respiratory air flows through the connection line 2 and through the valve seat 27 of the double membrane valve 3 opened by the switch membrane 26 into the gas supply line 5 and from there into the air bag 6. The pivoting wall 8 is prestressed by the pressure spring 13 and is pushed into the direction of the inspiration arrow 32, so that respiratory air from the air bag 6 reaches the inhalation connection 18 of the mask carrier through the inhalation line 17. By means of the prestress a compression of the air bag 6 is achieved and therefore a minor pressure during the inspiration.

The contour of the cam plate 15 which is connected torsionally rigid to the movable pivoting wall 8 is designed so that a constant prestress is exerted at the inhalation line 17 independent of the filling volume of the air bag 6.

During the inspiration phase the pneumatic adjusting element 4 is in the upper position of the membrane 29 (shown in a broken line) so that no additional releasing force working against the action of the pressure spring 13 is exerted by means of the mechanical coupling element 30.

At the beginning of the expiration phase exhalation air from the exhalation connection 19 is fed into the branched supply line 20. The dynamic pressure generated herein upstream of the $CO_2$ absorber 21 propagates or is transmitted via the feed line 20 to one side of the control membrane 23. Its other side is admitted with pressure from the interior of the air bag 6 by way of the pressure control line 24. According to the differential pressure occurring herein the control membrane 23 adjusts the check block 25 connected to it, and the switch membrane 26 is pushed into the sealing position, so that the respiratory air supply by means of the connection line 2 and the gas supply line 5 into the air bag 6 is suspended. The pressure in the connection line 2 increases and the dynamic pressure propagates into the extension chamber 28 upstream of the membrane 29 of the pneumatic adjustment element 4. By this means the mechanical coupling element 30 in the shape of a toothed rod engages with a toothed ring or pear 38 arranged around the axis of the pivoting wall 8. The wall 16 is adjusted so that a counter force to the mechanical prestress from the pressure spring 13 through the pull connection 14 becomes effective. Thus the expansion of the air bag 6 is supported and exhalation is facilitated.

The respective process movements are represented by means of the expiration arrow.

In the described closed-cycle gas mask and breathing equipment a breathing support in the inspiration phase is achieved by a prestress working on the movable pivoting wall 8 and in the expiration phase by means of the pneumatic adjustment element 4, whose mechanical coupling element 30 opposes the spring action of the pressure spring 13.

In any case, however, it is guaranteed that the pressure in the respiratory cycle cannot fall short of a predetermined set value either in the inspiration phase or in the expiration phase, so that a safe seal against the intrusion of pollutants is maintained.

While specific embodiments of the invention have been shown and described in detail to illustrate the application of the principles of the invention, it will be understood that the invention may be embodied otherwise without departing from such principles.

What is claimed:

1. A closed cycle breathing apparatus, comprising:
a pressurized air source;
a bellows-type breathing bag;
an inspiration line connected to said breathing bag;
an expiration line connected to said breathing bag; prestress means for applying a force to said breathing bag for contracting said breathing bag to urge air out of said breathing bag;
control means for counter-acting said prestress means allowing expansion of said breathing bag during expiration including a pneumatic control valve means connected to said exhalation line and connected to said breathing bag for responding to a difference between gas pressure in said exhalation line and gas pressure in said breathing bag for switching between an inspiration phase and an expiration phase based on said difference and for connecting said pressurized breathing source with said air bag during the inspiration phase and interrupting the connection between said pressurized air source and the breathing bag during the expiration phase and for actuating a pneumatic adjustment element during the expiration phase for offsetting the force applied by said prestress means.

2. A closed cycle breathing apparatus according to claim 1 wherein said prestress means includes a spring element for the generation of a prestress force on said breathing bag.

3. A closed cycle breathing apparatus according to claim 2, wherein said breathing bag has a moveable pivoting wall connected to said spring element.

4. A closed cycle breathing apparatus according to claim 3, wherein said prestress means includes transmission means for transmission of force from said wall to said spring element including a curved plate with a connection element extending around said curve plate, said connection element acting on said wall so as to insure that said supply pressure of said breathing bag is at least approximately constant independently of its filling volume.

5. A closed cycle breathing device and gas mask according to claim 4, wherein said wall is connected to a counterbalance weight.

6. A closed cycle breathing apparatus according to claim 1, wherein said pneumatic control valve comprises a double membrane valve including a control membrane transmitting a differential pressure between pressure in said exhalation line and pressure in said breathing bag, and a switch membrane means operatively connected to said control membranes for switching pressurized air flow between the breathing bag and said pneumatic adjustment element based on the position of said control membrane.

7. A closed cycle breathing apparatus according to claim 3, wherein said expiration line is in fluid communication with said breathing bag such that an exhalation pressure acts as dynamic pressure on an interior surface of said moveable pivoting wall.

8. A closed cycle breathing apparatus according to claim 3, wherein said pneumatic adjustment element is provided for transferring a moment to the pivoting wall by means of a mechanical coupling element to oppose the force applied by said spring element.

9. A closed cycle breathing apparatus according to claim 8, wherein said pneumatic adjustment element has an expansion chamber which is closed on one side by an adjustment membrane, said moveable pivoting wall having a pivot point, a tooth wheel carried at said pivot point and being rotatable with said wall, a tooth rod engaged with said toothed wheel and engaging said adjustment membrane and being actuatable thereby to rotate said tooth wheel to change the position of said wall.

10. A closed cycle breathing apparatus according to claim 1 wherein said air source includes smoothing means for smoothing pressure peaks comprising a throttle in a main flow line and a pressure release valve branching off from said throttle.

11. A pressure operated closed cycle breathing device, comprising a respiratory gas supply under pressure, a bellows member air bag having a fixed wall with inner and outer ends, a movable wall pivotally supported adjacent said inner end of said fixed wall and having a movable wall outer end, a bellows member connected between said fixed wall outer end and said moveable wall outer end and enclosing a space, an inhalation line connected to said air bag space, an exhalation line connected to said air bag space, control means connected to said respiratory gas supply, said control means including an interior portion a diaphragm means within said interior portion dividing said interior into a first space connected to said air bag space and a second space connected to said exhalation said diaphragm means line for sensing a pressure difference between said exhalation line and said air bag space and for connecting said respiratory gas supply to said air bag space in dependence upon the pressure difference sensed, mechanical coupling means having a mechanical adjusting element connected to said movable wall to move said movable wall during exhalation and connected to said respiratory gas delivery line and responsive to pressure in said line delivery to aid in moving said movable wall.

* * * * *